United States Patent [19]

Genna et al.

[11] Patent Number: 4,831,261

[45] Date of Patent: * May 16, 1989

[54] COMPOUND COLLIMATOR AND TOMOGRAPHY CAMERA USING SAME

[75] Inventors: Sebastian Genna, Belmont; Andrew P. Smith, Medford, both of Mass.

[73] Assignee: Digital Scintigraphics, Inc., Cambridge, Mass.

[*] Notice: The portion of the term of this patent subsequent to Nov. 1, 2005 has been disclaimed.

[21] Appl. No.: 34,702

[22] Filed: Apr. 6, 1987

Related U.S. Application Data

[63] Continuation-in-part of Ser. No. 876,811, Jun. 20, 1986, Pat. No. 4,782,233.

[51] Int. Cl.[4] .................................................. G01T 1/20
[52] U.S. Cl. ............................ 250/363.01; 250/505.1; 250/363.04
[58] Field of Search ............... 250/363 SH, 369, 505.1

[56] References Cited

U.S. PATENT DOCUMENTS 4,389,569  6/1983  Hattori et al. ............... 250/363 SH
4,584,478  4/1986  Genna et al. ................ 250/363 SH

FOREIGN PATENT DOCUMENTS 1159179  7/1986  Japan ........................... 250/363 SH
1159180  7/1986  Japan ........................... 250/363 SH Primary Examiner—Carolyn E. Fields
Assistant Examiner—John A. Miller
Attorney, Agent, or Firm—Joseph S. Iandiorio; Douglas E. Denninger

[57] ABSTRACT

A compound collimator for use in a radionuclide emission tomography camera to image a region of an object, including a collimator structure having a number of collimator elements arranged in at least two sections to define a different tomographic field of view boundary for each section. Each boundary encompasses a different portion of the region and the sections in combination establish a different imaging sensitivity for each portion. At least one of the boundaries encompasses the entire region to be imaged.

29 Claims, 11 Drawing Sheets

COMPOUND COLLIMATOR AND TOMOGRAPHY CAMERA USING SAME

RELATED APPLICATIONS

This application is a continuation-in-part of U.S. Pat. Ser. No. 876,811, now U.S. Pat. No. 4,782,233 Genna et al., Multifield Collimator System and Method and Radionuclide Emission Tomography Camera Using Same, filed June 20, 1986.

FIELD OF INVENTION

This invention relates to the imaging of objects by radionuclide emission tomography and more particularly to the collimation of emission signals in radionuclide emission tomography cameras to obtain different imaging sensitivities utilizing a compound collimator.

BACKGROUND OF INVENTION

Conventional radionuclide emission tomography cameras construct three-dimensional images of an object's radionuclide distribution from a sequence of two-dimensional images collected through one or more collimators from a large number of viewing angles around the object being imaged. The very nature of the image reconstruction process, that is, the underlying mathematical theory and associated computer reconstruction algorithms, is such that in a preferred construction a tomographic field of view in the camera system encompasses the entire object being imaged. A tomographic field of view is the enclosed region of a field defined by the intersections of one or more collimator fields of view as the collimators rotate about the object of view through $2\pi$ radians. Failure to include the entire imaged object in a tomographic field of view results in insufficient information to uniquely reconstruct its three-dimensional radionuclide distribution.

When a rotating planar radionuclide camera is employed to collect the images for reconstruction, a single continuous multi-parallel hole (channel) or converging hole collimator, having a field of view encompassing the object, is used in order to restrict emissions received by the camera detector from the object to those gamma rays following parallel or diverging projections toward the detector. In the case of stationary annular camera detector with rotating collimator, disclosed for example by the patents of Hattori et al., U.S. Pat. No. 4,389,569, and Genna et al., U.S. Pat. No. 4,584,478, a rotating annular collimator system is segmented into a multiplicity of either parallel hole or converging hole collimator segments; however, each of these collimator segments still has a tomographic field of view as large as, or larger, than the imaged object, and provides only one such field of view.

A shortcoming of both of these systems is that the imaged object's radionuclide distribution is sampled either with uniform efficiency in the case of the parallel hole collimator or, in the case of the annular camera with rotating converging hole collimator, the center of the tomographic field of view is sampled with a lower efficiency than the periphery. Experimental studies of the effect of uniform sampling (Pang, S. C. and Genna, S., "Noise Propagation in 3-D Fourier Convolution Reconstruction" in *Image Processing for 2-D and 3-D Reconstruction from Projections*, Optical Society of America, PD-11, 1975) using a uniformly emitting water phantom have shown a substantial increase in the variance per pixel or decrease in the signal-to-noise ratio of the reconstructed data near the central portion of the imaged phantom. In clinical applications, however, the central regions of an imaged human body part are typically those in which enhanced imaging ability is desired, i.e., less variance in the measured data.

SUMMARY OF INVENTION

It is therefore a primary object of this invention to improve the imaging sensitivity of radionuclide emission tomography cameras in portions of an imaged object exhibiting the greatest clinical interest.

It is a further object of this invention to enhance camera efficiency in one or more portions of the imaged object by constructing a collimator to provide greater imaging sensitivity in those portions.

Yet another object of this invention is to provide an improved collimator which provides both greater imaging sensitivity and greater inherent resolution in selected portions of the object.

It is a further object of this invention to provide such a collimator which is smaller in size than conventional collimators providing uniformly higher sensitivities.

It is a further object of this invention to provide such a collimator which enables more efficient use of an associated detector.

A still further object of this invention is to provide a method of constructing a compound collimator.

This invention results from the realization that the truly effective collimation of radionuclide emissions from a region of an object can be achieved by imaging the region with a collimator constructed to have at least two sections of collimator elements which establish different imaging sensitivities for different portions of the region, each portion being bounded by a tomographic field of view boundary corresponding to one or more of the sections, to provide greater imaging sensitivities in the portions of greatest clinical interest while reducing the overall size of the collimator.

This invention features a compound collimator for use in a radionuclide emission tomography camera to image a region of an object. There is a collimator structure having a plurality of collimator elements arranged in at least two sections to define a different tomographic field of view boundary for each section. Each boundary encompasses a different portion of the region and the sections in combination establish a different imaging sensitivity for each portion. At least one of the boundaries encompasses the entire region to the imaged.

In one embodiment, the sections define nonoverlapping tomographic fields of view. One of the sections is divided into two parts, one part being disposed on each side of the other section. The collimator structure may be a planar collimator and be linearly symmetric about the non-divided section. Alternatively, the collimator structure is curvilinearly symmetric about the center of the non-divided section. The collimator elements are continuous throughout the collimator structure and are contiguous to each other.

In another embodiment, the sections define at least one boundary which encompasses the entire object. At least one of the sections may exhibit uniform imaging sensitivity throughout the section; alternatively, at least one of the sections exhibits non-uniform imaging sensitivity throughout the section. One or more of the sections may be a parallel type collimator, a converging type collimator, or a diverging type collimator. The collimator structure may be an annular rotating collimator.

In yet another embodiment, the collimator structure is rotatable about an axis of rotation and the boundaries are concentric about the axis of rotation. The sections define the boundaries as closed curves. The collimator structure may be a planar or arcuate collimator which is translatable toward or away from the region. The compound collimator may further include at least one separate collimator segment defining a tomographic field of view boundary which also encompasses a portion of the region. The separate collimator segment overlaps with part of the tomographic field of view of at least one of the sections and provides increased sensitivity in the area of overlap.

This invention also features a radionuclide emission tomography camera for imaging a region of an object, including a compound collimator having at least two sections, means responsive to the compound collimator for detecting radionuclide emissions from the region to collect at least one collimated image through each collimator element. The camera further includes means for combining the collimated images to produce a final image of the region exhibiting imaging sensitivities which differ for the two portions.

In one embodiment, the camera further includes means for rotating the compound collimator about an axis of rotation, the boundaries are concentric about the axis, and the means for rotating moves the compound collimator to successive positions about the region. The means for combining includes means for matching together the images collected at the same position by adding together collimated images collected at each position through the compound collimator.

This invention further features a method of constructing a compound collimator for use in a radionuclide emission tomography camera to image a region of an object, including defining at least two tomographic field of view boundaries within the region, each boundary encompassing a different portion of the region and at least one boundary encompassing the entire region. The method further includes selecting a different imaging sensitivity for each portion of the region, and constructing for each boundary a section of a collimator structure. Each section has a plurality of collimator elements arranged within each section to establish the selected imaging sensitivity for each defined portion.

In one embodiment, defining includes determining an axis of rotation about which the collimator structure is rotatable, and constructing includes selecting a first distance between the axis of rotation and the edge of the collimator structure. Constructing further includes establishing a different focal length for each section.

DISCLOSURE OF PREFERRED EMBODIMENTS

Other objects, features and advantages will occur from the following description of a preferred embodiment and the accompanying drawings, in which.

This invention may be accomplished by a collimation system for use with a radionuclide emission tomography camera, having a collimator structure which is organized in at least two sections each of which defines a different tomographic field of view boundary. Each boundary encompasses a different portion of the region to be imaged, and the sections in combination establish a different imaging sensitivity for each portion. At least one of the boundaries encompasses the entire region to be imaged. Compound collimators according to this invention are discussed below in relation to FIGS. 5-14.

Figure 1:
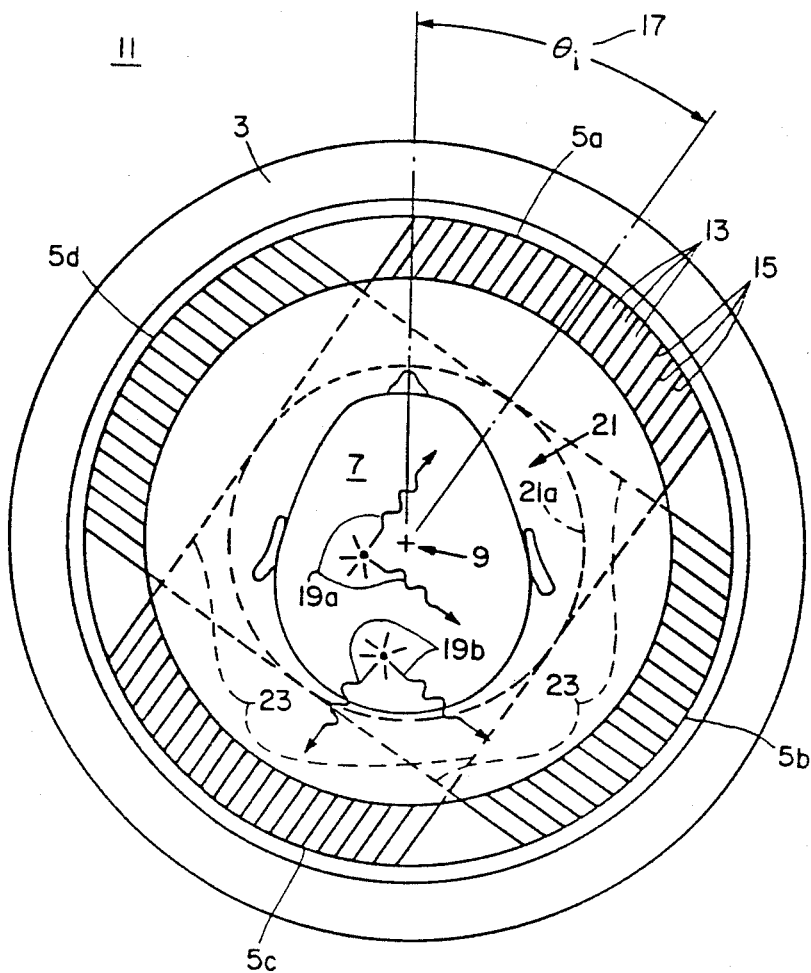
FIG. 1 is a schematic diagram of a conventional annular collimator system employing several parallel type collimator segments that illustrates the difference between the collimator field of view and the tomographic field of view, that is, the view within the boundary defined by the rotating collimator field of view.

There is shown in FIG. 1 a conventional collimator system consisting of several parallel type collimator segments 5a, 5b, 5c, 5d for use in annular radionuclide emission tomography camera 11. Each collimator segment has the same size field of view 23 as established by a multiplicity of equal hole size channels 13 separated by lead septa 15, and these fields of view are at least as wide as the breadth of the object 7 that is being imaged by position detector 3. The collimator segments 5a-5d rotate incrementally by angle 17 about axis of rotation 9, perpendicular to the page in FIG. 1, in order to generate a sequence of images surrounding the entire imaged object 7. This sequence of images is used to reconstruct the three-dimensional radionuclide distribution contained within imaged object 7. The mathematical theory and computer algorithms underlying the reconstruction process are such that the collimator segment field of view 23 must encompass the entire imaged object 7 at each of the angles 17 of view $\theta_i$.

There is also shown in FIG. 1 the tomographic field of view 21 having a boundary 21a which is defined as the intersection of the individual collimator segment fields of view 23 as the collimator segments 5a–5d rotate continuously through 360 degrees about axis of rotation 9. Only radionuclide distributions contained within the tomographic field of view 21 can be uniquely reconstructed into three-dimensional images; boundary 21a of tomographic field of view 21 represents the outermost radial position in relation to axis of rotation 9 of imaging of which camera 11 is capable. In the system of FIG. 1 four collimator segments 5a, 5b, 5c, 5d exhibit the same size segment field of view 23 and the same tomographic field of view 21. The sampling efficiency of this system is therefore the same throughout the tomographic field of view. In practice, however, radionuclide emission signals (gamma rays) 19a from the central portions of imaged object 7 typically travel through a greater thickness of the imaged object than emission signals 19b from the peripheral regions of the imaged object. Emissions produce gamma radiation 19a, 19b isotropically in the region surrounding the emission event, but such isotropy is not illustrated in FIG. 1 for clarity. Signals 19a from the central portion of imaged object 7 are thus detected by detector 3 with a lower signal-to-noise ratio than those from the peripheral regions of imaged object 7.

Figure 2:
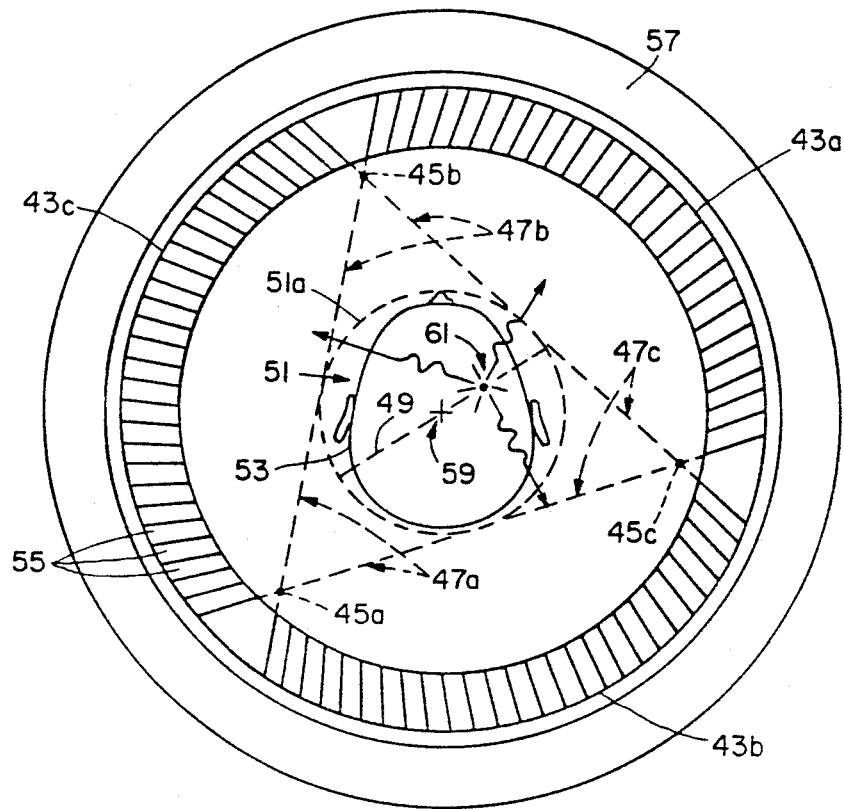
FIG. 2 is a sechematic diagram of a conventional annular collimator system employing several converging type collimator segments.

FIG. 2 shows a conventional annular collimator system 41 employing three collimator segments 43a, 43b, 43c of the converging type. For each collimator segment 43, the equal size collimator channels 55 converge, respectively, to a point 45a, 45b, 45c located beyond axis of rotation 59. The individual collimator segment fields of view 47a, 47b, 47c, all the same size in this case, produce a single overlapped tomographic field of view 51 having boundary 51a as each segment rotates through 360 degrees about axis 59 that encompasses the entire imaged object 53. The system 41 of FIG. 2 illustrates a conventional implementation used in an annular radionuclide tomography camera. If the converging collimators have uniform hole dimensions, the composite response of position detector 57 to an emission event 61 positioned along a diameter 49 of the tomographic field of view 51 increases with increasing radial displacement of event 61 from axis of rotation 59 as the collimator segments rotate 360° about axis 59. Thus, in the absence of attenuation, an emission event 61 whose location along diameter 49 is further from axis 59 will result in a larger composite signal (that is, the sum of signals produced by the complete set of collimator segments 43a, 43b, 43c) than an event whose location is closer to axis 59. Although FIG. 2 illustrates a conventional collimator system employing three collimator segments 43, any number of such segments may be employed.

Figure 3:
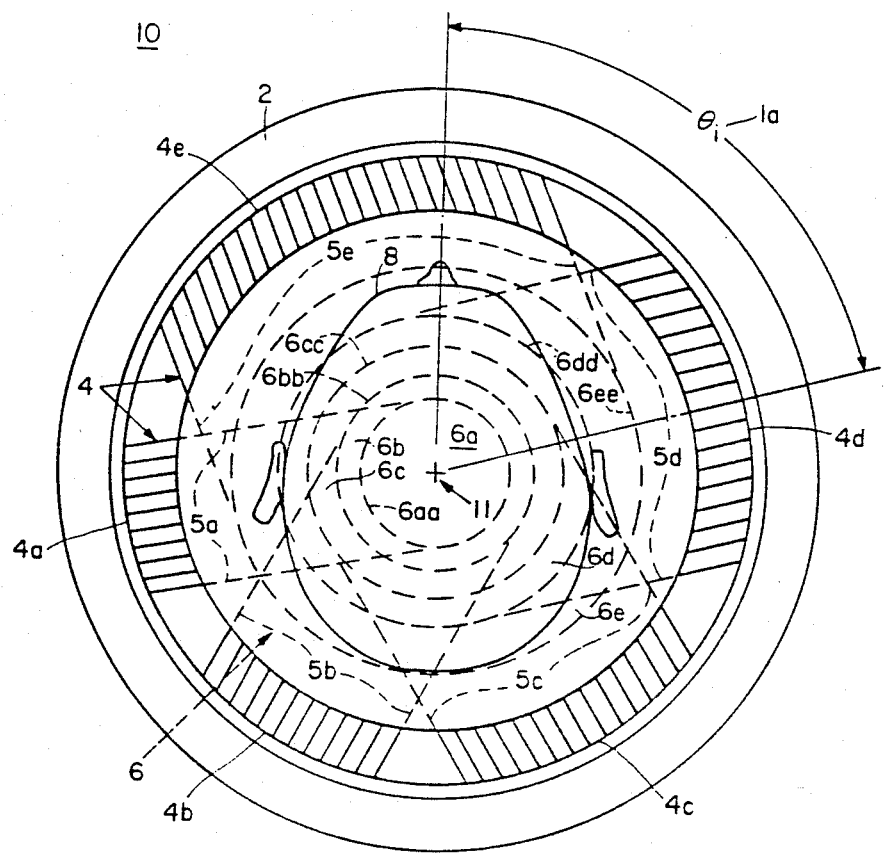
FIG. 3 is a schematic diagram of a novel multifield annular collimator system employing several parallel type collimator segments with different fields of view in which one of the collimator segments defines a tomographic field of view having a boundary which encompasses the object.

There is shown in FIG. 3 a collimator system 10 for a novel annular radionuclide emission tomography camera. The camera comprises a scintillation position detector 2 and collimator segments 4. Scintillation detector 2 consists of means for detecting the positions of scintillations produced by gamma rays emitted by radionuclides contained within the imaged object 8. Collimator segments 4a, 4b, 4c, 4d and 4e accept emission signals only from sources within their respective collimator fields of view 5a, 5b, 5c, 5d and 5e. An image from each collimator segment centered at one of a number of view positions such as position 1, shown at the angle 1a of view $\theta_i$, is combined with other images obtained at that position from the remaining collimator segments when they are rotated to that angle of view to develop a composite image of object 8 for each view position. The imaged object 8 in FIG. 3 is shown as a human head whose radionuclide distribution is being imaged for three-dimensional reconstruction by the radionuclide emission camera system of which collimator system 10 is a part. The entire disclosure of the following U.S. Patents are incorporated herein by reference, including their disclosures of radionuclide emission camera systems: U.S. Pat. Nos. Genna et al., 4,095,107; Genna et al., 4,228,515; Genna et al., 4,584,478; and Pang et al., 4,593,198.

Tomographic fields-of-view 6a, 6b, 6c, 6d, 6e having boundaries 6aa, 6bb, 6cc, 6dd, 6ee, respectively, are formed as a result of multiple viewing by collimator segments 4a, 4b, 4c, 4d, 4e, during tomographic imaging as the collimator is rotated through 2 radians. Tomographic fields of view 6a–6e overlap and in this construction are concentric since segments 4a–4e share the same axis of rotation 11. Gamma ray emissions occurring within the overlapping tomographic fields of view 6a, 6b, 6c, 6d of collimator segments 4 as defined earlier are imaged with enhanced efficiency or sensitivity. Thus, the central tomographic field of view 6a in FIG. 3 in which all five tomographic fields of view 6 overlap is imaged with greater efficiency than any of the other overlapping fields of view. The next central tomographic field of view, 6b, for example, is fully imaged only by four of the five collimator segments 4, and therefore the imaging efficiency or sensitivity in field of view 6b is less than that of view 6a.

Although five collimator segments 4 with five different tomographic fields of view 6 are shown in FIG. 3, this is not an inherent limitation. Any number of collimator segments greater than one may be used, and the tomographic fields of view may be of any desired spatial extent relative to the imaged object 8, as long as at least one boundary of the tomographic fields of view encompasses the imaged object. To uniquely reconstruct the three-dimensional radionuclide distribution in an object, at least one tomographic field of view boundary must encompass the entire object as the collimator system is rotated through $2\pi$ radians. However, it is known in the art to perform incomplete sampling which does not uniquely reconstruct the image but still provides useful information. Partial rotation of a collimator system according to this invention produces at least two incomplete tomographic fields of view each having an incomplete outer boundary which is not a closed curve. Useful information may still be obtained from the incomplete tomographic fields of view depending on the accuracy desired. Similarly, incomplete enclosure by the outermost boundary of the entire object, e.g., encompassing as a region all or a portion of the brain itself but not the skull of a patient, may also provide useful information and is also within the scope of this invention. The phrase "encompass the region to be imaged" hereinafter includes encompassing only that portion of the object which the observer wishes to image, whether or not the object in its entirety is encompassed.

Further, the collimator segments 4 may be of any type, parallel, the type shown in FIG. 3, converging or diverging. A parallel type collimator segment is one whose axis of convergence for imaged emission signals lies along an axis infinitely far from the collimator segment. A converging type collimator segment is one whose axis of convergence lies along an axis positioned at some point in the half-space containing the collimator segment and the emission source, but not at the point at infinity. And, a diverging collimator segment is one whose axis of convergence lies at some point outside the half-space containing the emission source and the collimator segment, but not at the point at infinity. The three types of collimator segments, parallel, converging, and diverging, are well-known in the art, and are frequently described as collimator segments with "infinite," "positive" and "negative" focal lengths, respectively. Hereinafter these different terminologies may be used interchangeably or in mixed form in order to describe various types of collimator segments.

Figure 4:
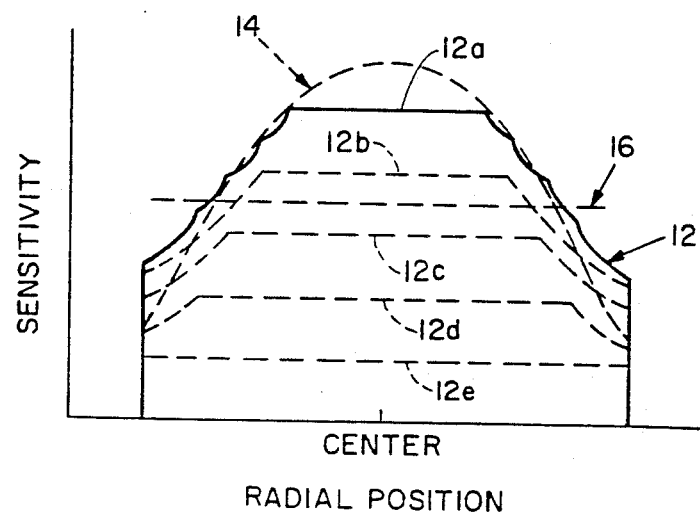
FIG. 4 is a graph of the relative sensitivity distribution (relative sampling efficiency as a function of radial position in the tomographic field of view) for a multifield collimator system employing parallel-hole uniform-sensitivity collimator segments.

FIG. 4 illustrates the relative sensitivity variation as a function of radial position in the tomographic field-of-view for several different types of collimator structures. The sensitivity distribution is a composite of collimated images centered as the same position, e.g., position 1, FIG. 3. One or more collimators that image the entire field of view uniformly exhibit the response shown in dashed curve 16, FIG. 4. Because different emission source points in the typical imaged object result in varying signal propagation path lengths through the imaged object, a uniform response curve such as curve 16 leads to a signal-to-noise ratio in the reconstructed image that decreases in central regions where the path length for emission signals is lower. This feature of typical radionuclide emission tomography cameras may be mitigated by varying the imaging sensitivity as a function of radial position in such a manner that it is increased in regions where the emission signal path length through the imaged object is longer.

An idealized non-uniform sensitivity curve 14 is shown in FIG. 4 in which maximum sensitivity occurs at the center of the imaged object. In order to achieve a continuously varying sensitivity curve such as curve 14, however, an infinite number of infinitely small collimator segments is required. In a practical collimation system, of course, only a finite number of collimator segments can be used, with the result that only an approximation to idealized curve 14 can be obtained. Continuous curve 12 in FIG. 4 illustrates a typical approximation to curve 14 achievable with a finite number of collimator segments as, for example, in the system of FIG. 3. Each collimator segment exhibits a uniform sampling efficiency, and the cumulative effect of imaging certain portions of the imaged object with overlapping tomographic fields of view from the several collimator segments is shown qualitatively in curve 12. For example, referring again to FIG. 3, collimator segment 4e with the largest tomographic field of view 6e images with uniform sensitivity 12e in FIG. 4. Collimator segment 4d in FIG. 3 with tomographic field of view 6d images its smaller field of view with the same efficiency as collimator segment 4e, with the result that the combined imaging sensitivity in tomographic field of view 6d is greater than it is in tomographic field of view 6e, as shown in curve 12d of FIG. 4. By similarly combining the uniform sensitivities of multifield-of-view collimators, the cumulative sensitivity distribution 12 is obtainable.

By using collimators with different tomographic fields of view, varying sensitivities (uniform or non-uniform), and different types (parallel, converging and diverging) many continuous sensitivity distributions can be acheived as an approximation to virtually any desired continuous radial sensitivity distribution. Thus, in regions of particular interest in the imaged object, the sensitivity can be increased with respect to its value in other areas, thus increasing the signal to noise ratio in the measured data.

Figure 5:
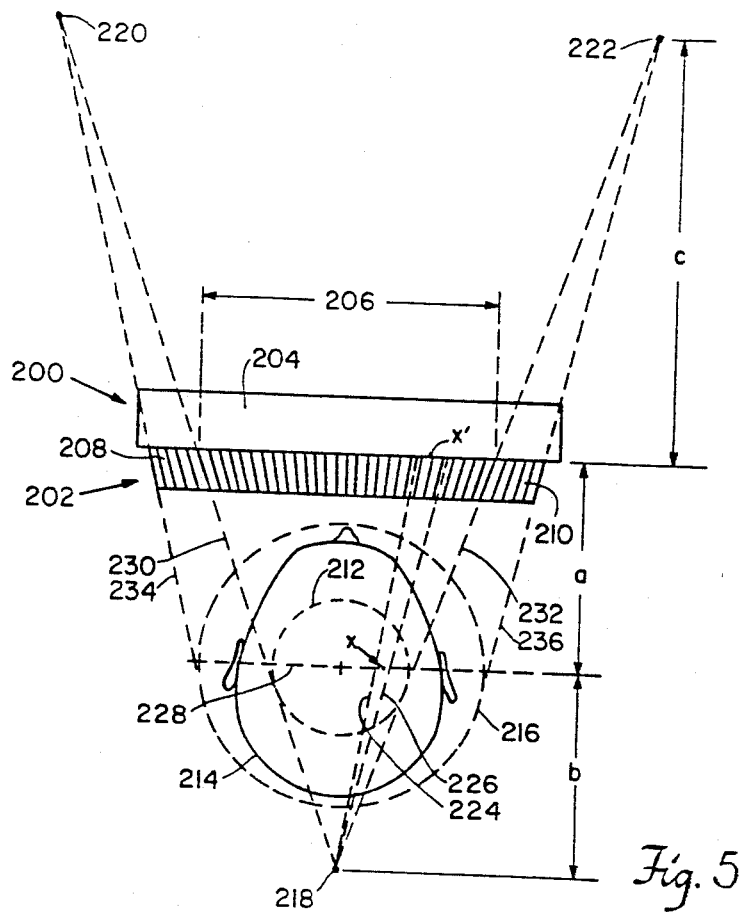
FIG. 5 is a schematic diagram of a compound collimator system according to this invention having two sections which define nonoverlapping tomographic field of view boundaries.

Compound collimator system 200, in FIG. 5, includes collimator structure 202 behind which is located position detector 204. Collimator structure 202 is divided into central converging section 206 which is bounded by a second, divided section composed of sections 208, 210 which are diverging collimators. Section 206 has a tomographic field of view which defines inner tomographic field of view boundary 212 about the inner portion of head 214. Diverging sections 208, 210 define tomographic field of view boundary 216 which encompasses head 214. Converging section 206 focuses positively to point 218 while diverging sections 208, 210 focus negatively to points 220, 222, respectively.

Converging section 206 provides both greater sensitivity and greater inherent resolution which is illustrated as follows. Length x, located between dashed lines 224, 226 at the intersection of line 228 which is a diameter line passing through axis of rotation 230, is magnified to length x' at distance a, corresponding to the forward face of detector 204. Focal point 218 of converging section 206 is distance a+b from detector 204. Projections along diameter line 228 within tomographic field of view boundary 212 are magnified by the ratio of their respective distances, that is, by (a+b)/b.

Both sensitivity and inherent resolution are improved proportionally to the magnification defined by the above ratio. In the absence of attenuation, the sensitivity of a tomography camera is proportional to the fraction of radiation received by the camera of the total radiation emitted from the radionuclide source distribution. The inherent resolution, or effective intrinsic resolving power, is the ability of the detector to resolve two events striking its surface.

While a converging collimator improves both sensitivity and inherent resolution, the converging collimator is by its nature much larger in size than that of a corresponding parallel collimator, such as is evident by comparing parallel collimator 5a, in FIG. 1, with converging collimator 43a, in FIG. 2. Further, the detector must be correspondingly large to gather the collimated data. Compound collimator 202 achieves high imaging sensitivity within tomographic field of view boundary 212 while minimizing the length of detector 204 by imaging the remaining portion of head 214 utilizing diverging collimator sections 208, 210.

One technique of constructing compound oscillator 202 is as follows. Tomographic field of view boundaries 212, 216 are defined such that boundary 212 encompasses a portion to be imaged at a greater imaging sensitivity, and boundary 216 is defined to encompass head 214 which is the object to be imaged. The selected imaging sensitivity for converging section 206 determines focal point 218; section 206 is bounded by lines 230, 232 intersecting at focal point 218. To minimize the overall length of detector 204, boundary lines 230, 232 are extended negatively as are lines 234, 236 which are tangent to outer boundary 216. The boundary lines intersect at negative focal points 220, 222, respectively, at distance c from the forward face of detector 204. Along diameter line 228 between boundary lines 212 and 216, the magnification is equal to $c/(a+c)$.

The net sensitivity at any point within boundaries 212, 216 is given by the average of the sensitivities attributable to that point as collimator system 200 is positioned sequentially about axis of rotation 230. The collimator sections operate in combination: for example, collimator sections 108, 210 corresponding to the portion for which tomographic field of view boundary 216 is defined establish, in combination with the sections, e.g. section 206, having collimator fields of view overlapping that portion, a different imaging sensitivity for that portion. The inner collimator sections typically have collimator fields of view which overlap the fields of view of peripheral collimator sections.

Figure 6:
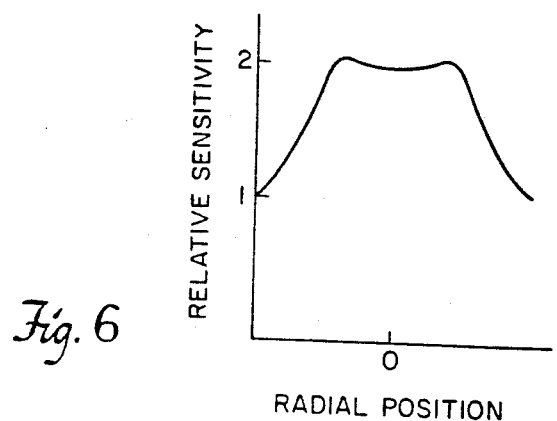
FIG. 6 is a graph of the relative sensitivity distribution for the compound collimator system of FIG. 5.

A sensitivity profile through diameter line 228 in relation to radial position is shown in FIG. 6. The circularly symmetrical sensitivity profile is highest in the central regions of the tomographic field of view and lowest at the periphery. Within boundary 212, which is viewed only by converging section 206, the sensitivity is nearly constant, varying between 2.0 and 2.1. Progressing radially outward thereafter, the sensitivity diminishes to approximately 55 percent of its peak value at the edge of boundary 216. In another construction in which diverging sections 208, 210 occupy a larger fraction of the total field, the sensitivity at the periphery will be even lower because the lower sensitivity diverging collimators contribute more strongly to the admixture of sensitivities at the edges of the field.

Computerized tomographic reconstruction from parallel projections is accomplished by rebinning of detector data collected at different viewing angles. The data collected at different viewing angles from a mixture of non-parallel projected gamma rays, that is, with converging and diverging collimators, is accomplished by reorganizing the data into sets of parallel projected data as is well known in the art.

Figure 7:
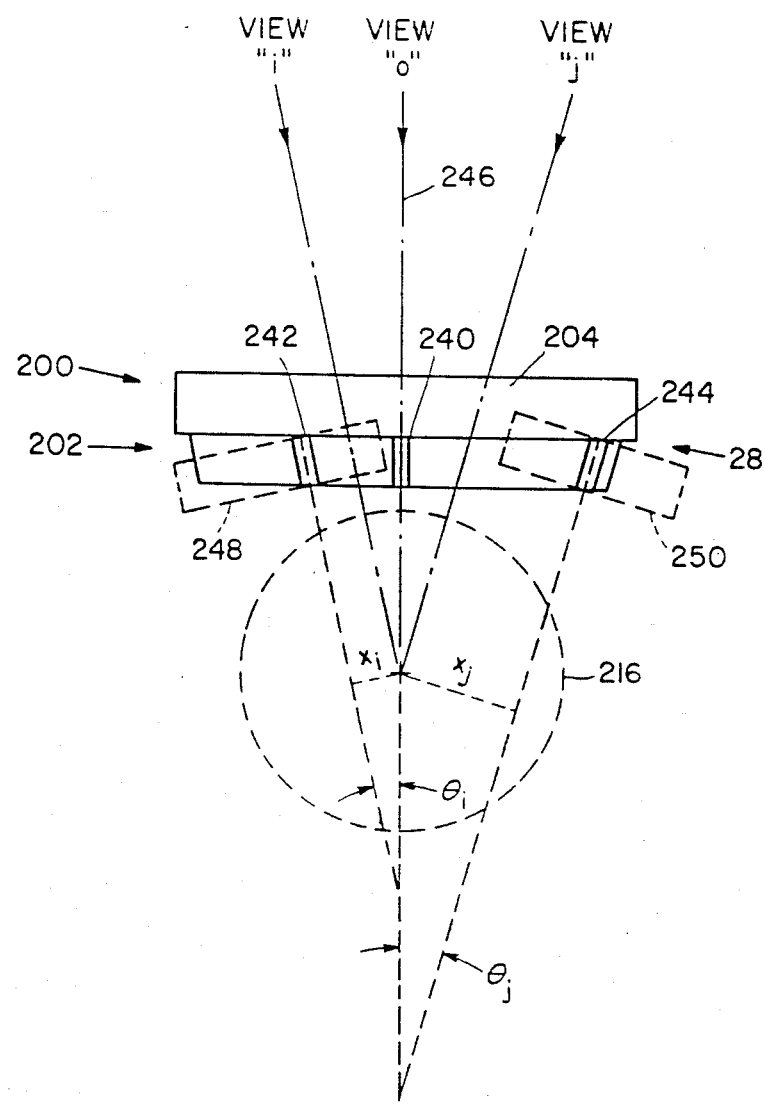
FIG. 7 is a schematic of the collimator system of FIG. 5 illustrating the organization of detector data for rebinning.
Figure 8:
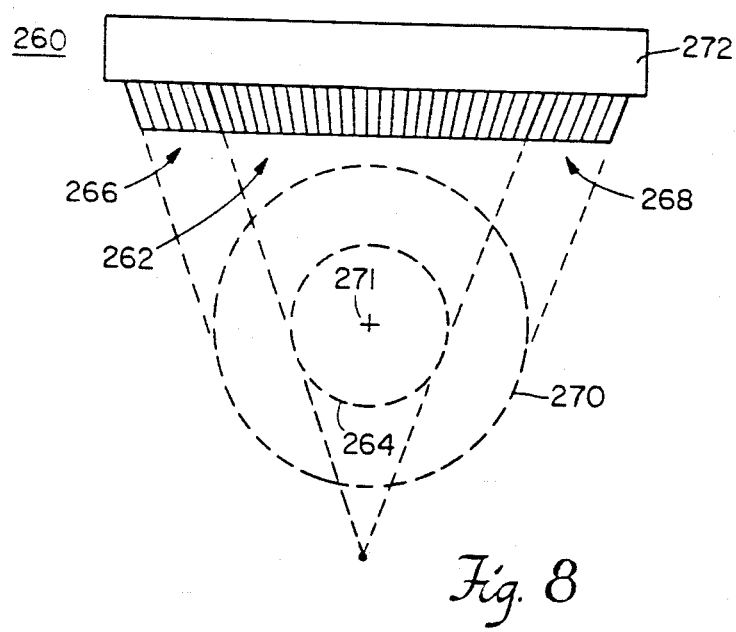
FIG. 8 is a schematic diagram of yet another compound collimator system according to this invention having a converging center section and a divided parallel collimator section on either side of the converging section.

Rebinning is illustrated in FIG. 7 for collimator elements 240, 242 within converging section 206 and collimator element 244 within diverging section 210. Collimator structure 202 is positioned at detector viewing position "0" with its center line 246 at $\theta=0$. At this position, all other collimator elements view within boundary 216 at a different angle. For example, collimator element 242 views the portion within boundary 216 at an angle $\theta_i$; the view position is represented by imaginary parallel collimator 248, shown in phantom. Similarly, diverging collimator element 244 views the portion within boundary 216 at view position $\theta_j$, represented by imaginary parallel collimator 250. Data collected through collimator elements 242, 244 therefore contribute to the $\theta_i$ and $\theta_j$ set of parallel projections at distances $x_i$ and $x_j$, respectively, from the central line of each imaginary parallel collimator. The various views are summed as collimator system 200 is rotated until all bins are filled.

Other compound collimators according to this invention have different combinations of collimator sections. Collimator systems 260, FIG. 8, incldes converging section 262 which defines boundary 264, and parallel collimator sections 266, 268 which define boundary 270. The sensitivity at the periphery is thereby increased relative to collimator system 200, FIG. 5, but a slightly larger positioned detector 272 is required to accommodate the added collimator surface as necessitated by parallel hole collimator sections 266, 268.

Boundaries 264, 270 need not be circular about axis of rotation 271. For example, in another construction, collimator system 260 is translatable radially relative to axis of rotation 271 to define boundaries 264, 270 which are no longer circular.

Figure 9:
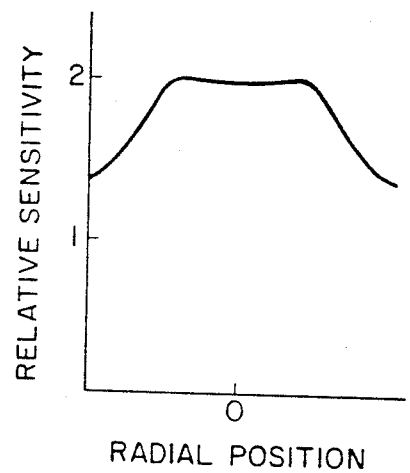
FIG. 9 is a graph of the relative sensitivity distribution for the collimator system of FIG. 8.

The relative sensitivity distribution for collimator system 260 is shown in FIG. 9. The sensitivity profile in the central region is approximately equal to that of collimator system 200, because similar converging collimator sections are utilized in both constructions. Toward the periphery, however, where the sensitivity is an admixture of collimator viewings, the sensitivity diminishes to about 67 percent of its central value.

Figure 10:
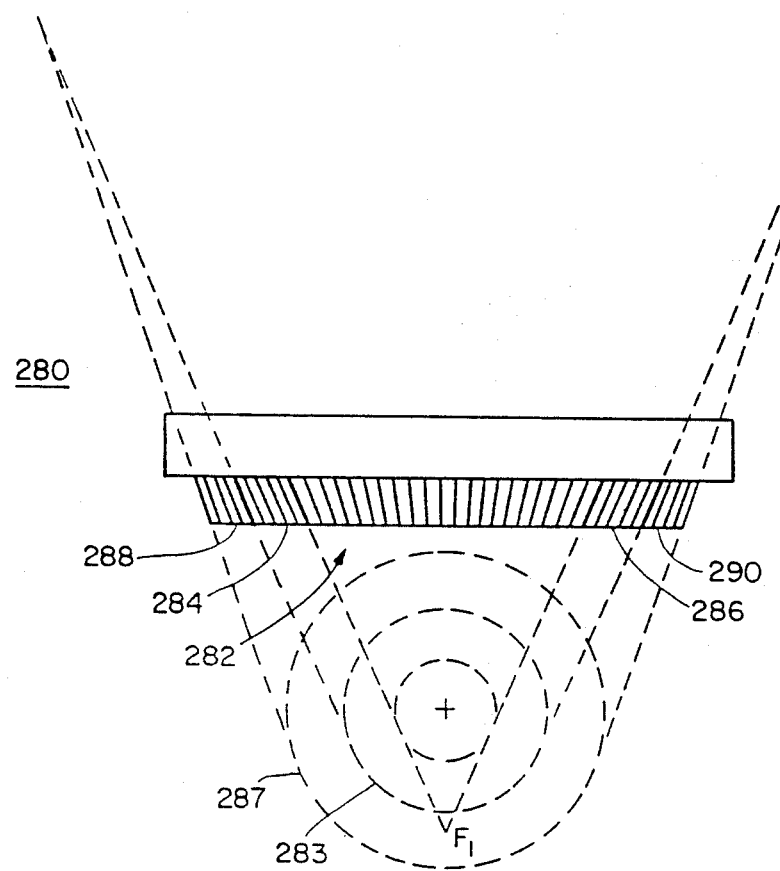
FIGS. 10-13 are schematic diagrams of yet other constructions of compound collimator systems according to this invention.

Collimator system 280, FIG. 10, utilizes three types of collimator sections. Central section 282 is highly converging which generates increased magnification and in turn provides increased imaging sensitivity and intrinsic resolution. Tomographic field of view boundary 283 is defined by parallel sections 284, 286, and outer boundary 287 is defined by diverging sections 288, 290.

The central collimator section of a compound collimator accoring to this invention need not be converging, and the region with the highest imaging sensitivity can lie in the outer portion of the object. Collimator system 300, for example, FIG. 11, has central parallel section 302 and outer converging sections 304, 306 which provide higher imaging sensitivities between boundaries 308, 310 for collimator system 300. The relative sensitivity is 1.0 within boundary 310 and increases toward the periphery.

Figure 12:
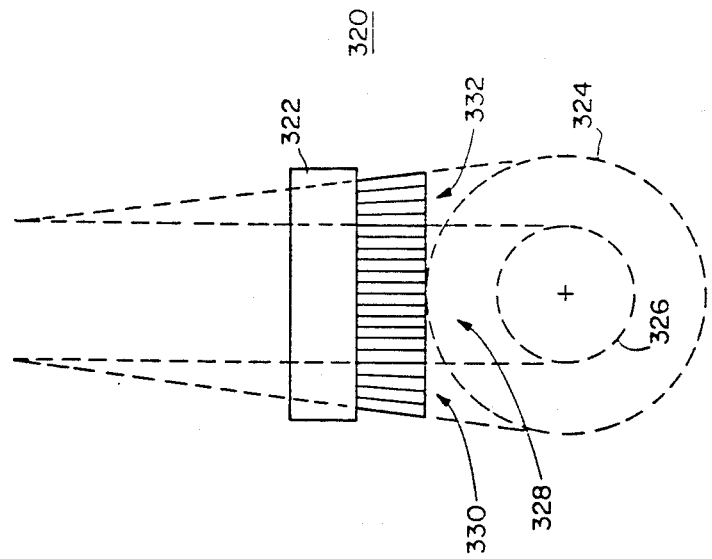
Figure 11:
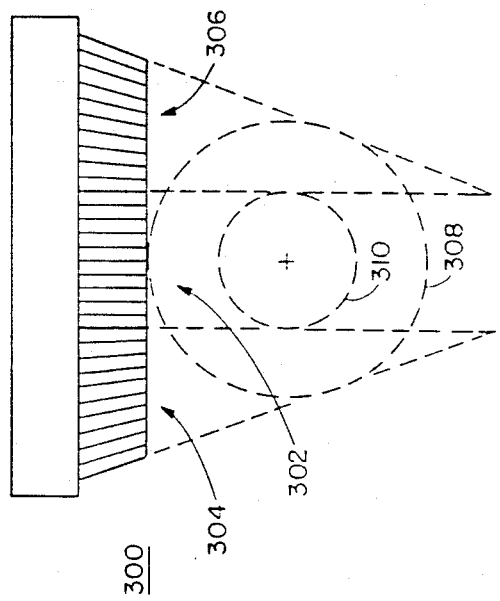

Collimator system 320, FIG. 12, utilizes detector 322 which is smaller than tomographic field of view boundary 324. Nonetheless, collimator system 320 achieves the viewing of the portion within boundary 326 at the imaging sensitivity of a parallel collimator. This is accomplished using central parallel section 328 and outer diverging sections 330, 332.

Figure 13:
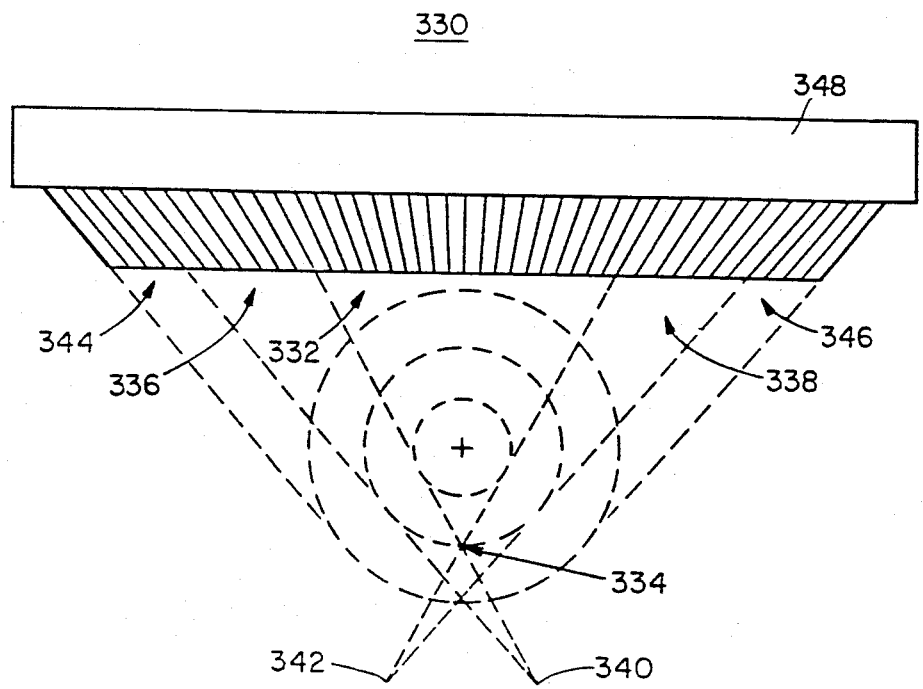

Very high imaging sensitivities are provided by collimator system 330, FIG. 13, having central strongly converging section 332 which focuses to point 334, and less strongly converging sections 336 and 338 which focus to points 340, 342, respectively. The outer portion of the region to be imaged is viewed by parallel sections 344, 346. Collimator system 330 is particularly useful when viewing a small object such as a brain, when a large position detector 348 can be accommodated.

Figure 14:
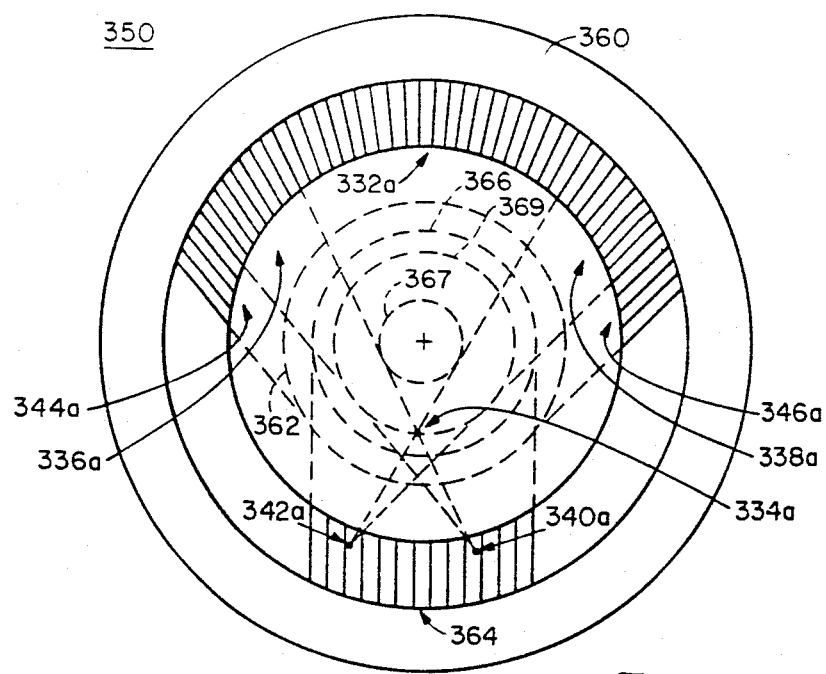
FIG. 14 is a schematic diagram of a compound collimator according to this invention combined with a separate collimator segment having an overlapping tomographic field of view.

Collimator system 350, FIG. 14, illustrates a modification of collimation system 330, FIG. 13, for use in a rotating annular collimator system with fixed position detector 360. Central converging section 332a focuses to point 334a, sections 336a, 338a focus to points 340a, 342a, respectively, and parallel sections 344a, 346a view the portion within outer tomographic field of view boundary 362. In addition, separate collimator segment 364 defines boundary 366 which overlaps boundaries 367, 369 defined by sections 332a, 336a, 338a, and part of the field of view of parallel sections 344a, 346a. Enhanced imaging sensitivity is provided in the region of overlap.

Figure 15:
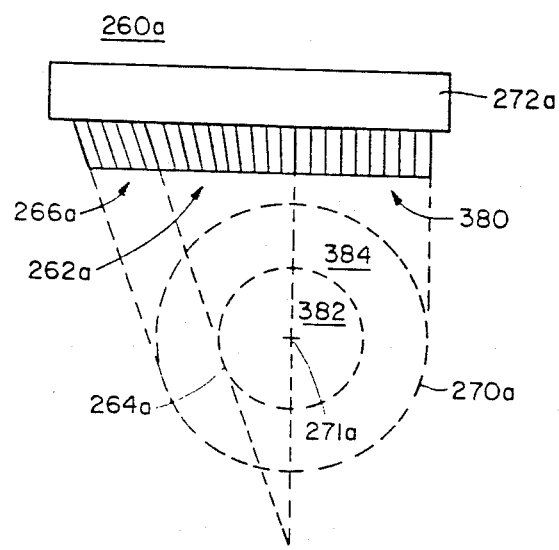
FIG. 15 is a schematic diagram of another compound collimator system according to this invention having asymmetric collimator sections.

Compound collimators according to this invention need not be symmetric. Collimator system 260a, FIG. 15, rotates about axis of rotation 271a and includes converging section 262a which defines boundary 264a, and parallel collimator section 266a which defines boundary 270a. In addition, collimator system 260a further includes parallel collimator section 380 which has a collimator field of view that overlaps both portions 382, 384 within boundaries 264a, 270a, respectively. Section 380 enables detector 272a to be shorter in length than detector 272, FIG. 8.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A compound collimator for use in a radionuclide emission tomography camera to image a region of an object, comprising a collimator structure having a plurality of collimator elements arranged in at least two sections to define a different tomographic field of view boundary for each section, each boundary encompassing a different portion of the region and the sections in combination establishing a different imaging sensitivity for each portion, and at least one of the boundaries encompassing the entire region to be imaged.

2. The compound collimator of claim 1 in which said sections define non-overlapping tomographic fields of view.

3. The compound collimator of claim 1 in which one of said sections is divided into two parts, one part being disposed on each side of the other section.

4. The compound collimator of claim 3 in which said collimator structure is a planar collimator and is linearly symmetric about the center of the non-divided section.

5. The compound collimator of claim 3 in which said collimator structure is curvilinearly symmetric about the center of the non-divided section.

6. The compound collimator of claim 1 in which said collimator elements are continuous throughout the collimator structure and are contiguous to each other.

7. The compound collimator of claim 1 in which said sections define at least one boundary which encompasses the entire object.

8. The compound collimator of claim 1 in which at least one of said sections exhibits uniform imaging sensitivity throughout said section.

9. The compound collimator of claim 1 in which at least one of said sections exhibits non-uniform imaging sensitivity throughout said section.

10. The compound collimator of claim 1 in which at least one of said sections is a parallel type collimator.

11. The compound collimator of claim 1 in which at least one of said sections is a converging type collimator.

12. The compound collimator of claim 1 in which at least one of said sections is a diverging type collimator.

13. The compound collimator of claim 1 in which said collimator structure is an annular rotatable collimator.

14. The compound collimator of claim 1 further including means for rotating said collimator structure about an axis of rotation.

15. The compound collimator of claim 14 in which said boundaries are concentric about said axis of rotation.

16. The compound collimator of claim 14 in which said sections define said boundaries as closed curves.

17. The compound collimator of claim 1 in which said collimator structure is a planar collimator.

18. The compound collimator of claim 17 further including means for translating said collimator structure toward or away from the region.

19. The compound collimator of claim 1 in which said collimator structure is an arcuate collimator.

20. The compound collimator of claim 19 further including means for translating said collimator structure toward or away from the region.

21. The compound collimator of claim 1 further including at least one separate collimator segment defining a tomographic field of view boundary which also encompasses a portion of the region.

22. A radionuclide emission tomography camera for imaging a region of an object, comprising:
a compound collimator having a plurality of collimator elements arranged in at least two sections to define a different tomographic field of view boundary for each section, each boundary encompassing a different portion of the region and the sections in combination establishing a different imaging sensitivity for each portion, and at least one of the boundaries encompassing the entire region;
means responsive to said compound collimator for detecting radionuclide emissions from the region to collect at least one collimated image through each collimator element; and
means for combining said collimated images to produce a final image of the region exhibiting imaging sensitivities which differ for the two portions.

23. The tomography camera of claim 22 further including means for rotating said compound collimator about an axis of rotation.

24. The tomography camera of claim 23 in which said boundaries are concentric about said axis of rotation.

25. The tomography camera of claim 23 in which said means for rotating moves said compound collimator to successive positions about the region and said means for combining includes means for matching together images collected at the same position.

26. The tomography camera of claim 25 in which said means for matching adds together collimated images collected at each position through said compound collimator.

27. A method of constructing a compound collimator for use in a radionuclide emission tomography camera to image a region of an object, comprising:
defining at least two tomographic field of view boundaries within the region, each boundary encompassing a different portion of the region and at least one boundary encompassing the entire region;
selecting a different imaging sensitivity for each portion of the region; and
constructing for each boundary a section of a collimator structure, each section having a plurality of collimator elements, and arranging the collimator elements within each section to establish the selected imaging sensitivity for each defined portion.

28. The method of claim 27 in which defining includes determining an axis of rotation about which the collimator structure is rotatable, and constructing includes selecting a first distance between the axis of rotation and the edge of the collimator structure opposite the object.

29. The method of claim 27 in which constructing includes establishing a different focal length for each section.

* * * * *

UNITED STATES PATENT OFFICE
CERTIFICATE OF CORRECTION

PATENT NO. : 4,831,261
DATED : May 16, 1989
INVENTOR(S) : Sebastian Genna, Andrew P. Smith It is certified that error appears in the above-identified patent and that said Letters Patent is hereby corrected as shown below:

Column 1, line 1, the following should be inserted:

-- This invention was made with Government support under Department of Health and Human Services Grant No. NS24609-03 awarded by the National Institute of Neurological and Communicative Disorders and Stroke. The Government has certain rights in the invention. --

Signed and Sealed this

Twenty-fourth Day of November, 1992

Attest:

DOUGLAS B. COMER

Attesting Officer

Acting Commissioner of Patents and Trademarks